United States Patent
Morise et al.

(10) Patent No.: US 11,864,905 B2
(45) Date of Patent: Jan. 9, 2024

(54) BIOLOGICAL FUNCTION MEASUREMENT AND ANALYSIS SYSTEM, BIOLOGICAL FUNCTION MEASUREMENT AND ANALYSIS METHOD, AND RECORDING MEDIUM STORING PROGRAM CODE

(71) Applicant: Ricoh Company, Ltd., Tokyo (JP)

(72) Inventors: Hirofumi Morise, Kanagawa (JP); Kiwamu Kudo, Ishikawa (JP); Yoshihiro Misaka, Ishikawa (JP); Eiichi Okumura, Ishikawa (JP); Tomoya Kimura, Ishikawa (JP); Yasuyuki Kawabuchi, Ishikawa (JP)

(73) Assignee: RICOH COMPANY, LTD., Tokyo (JP)

( * ) Notice: Subject to any disclaimer, the term of this patent is extended or adjusted under 35 U.S.C. 154(b) by 671 days.

(21) Appl. No.: 16/150,546

(22) Filed: Oct. 3, 2018

(65) Prior Publication Data
US 2019/0200912 A1    Jul. 4, 2019

(30) Foreign Application Priority Data
Dec. 28, 2017   (JP) .................................. 2017-254677

(51) Int. Cl.
*A61B 5/00*    (2006.01)
*G16H 40/60*    (2018.01)
(Continued)

(52) U.S. Cl.
CPC .............. *A61B 5/4064* (2013.01); *A61B 5/05* (2013.01); *A61B 5/242* (2021.01); *A61B 5/377* (2021.01);
(Continued)

(58) Field of Classification Search
CPC ......... A61B 5/242; A61B 5/05; A61B 5/4064; A61B 5/4094; A61B 5/7275; A61B 5/377; G01H 70/20
See application file for complete search history.

(56) References Cited

U.S. PATENT DOCUMENTS 7,123,955 B1    10/2006  Gao et al.
2004/0002635 A1    1/2004  Hargrove et al.
(Continued)

FOREIGN PATENT DOCUMENTS

CN    1420745 A    5/2003
CN    101589358 A    11/2009
(Continued)

OTHER PUBLICATIONS

Peirce, Jonathan W. "PsychoPy—psychophysics software in Python." Journal of neuroscience methods 162.1-2 (2007): 8-13.*
(Continued)

*Primary Examiner* — John D Li
(74) *Attorney, Agent, or Firm* — XSENSUS LLP

(57) ABSTRACT

A biological function measurement and analysis system, a biological function measurement and analysis method, and a recording medium storing program code causing a computer to execute the biological function measurement and analysis method. The biological function measurement and analysis system includes an input acceptance unit configured to accept selection of a biological function to be measured, and a measurement and analysis procedure determining unit configured to access a memory in which measurement and analysis procedure data, indicating a combination of measurement and analysis of reaction of a live subject caused by stimulation on a biological-function-by-biological-function basis, is stored to specify measurement and analysis procedure data corresponding to the selected biological function. The biological function measurement and analysis method
(Continued)

includes accepting the selection of biological function to be measured, accessing the memory, and specifying the measurement and analysis procedure data corresponding to the selected biological function.

13 Claims, 11 Drawing Sheets

(51) Int. Cl.
  *A61B 5/05* (2021.01)
  *A61B 5/242* (2021.01)
  *A61B 5/377* (2021.01)
  *G16H 50/30* (2018.01)
  *A61N 1/36* (2006.01)
(52) U.S. Cl.
  CPC .......... *A61B 5/4094* (2013.01); *A61B 5/4836* (2013.01); *A61B 5/7275* (2013.01); *G16H 40/60* (2018.01); *G16H 50/30* (2018.01); *A61N 1/36064* (2013.01)

(56) References Cited

U.S. PATENT DOCUMENTS

| | | | |
|---|---|---|---|
| 2004/0064066 A1* | 4/2004 | John | A61B 5/38 600/559 |
| 2004/0082847 A1 | 4/2004 | McDermott | |
| 2009/0099623 A1 | 4/2009 | Bentwich | |
| 2011/0092882 A1* | 4/2011 | Firlik | A61B 5/18 604/20 |
| 2011/0160796 A1 | 6/2011 | Lane et al. | |
| 2012/0277548 A1 | 11/2012 | Burton | |
| 2012/0302867 A1 | 11/2012 | Ichimura | |
| 2014/0148657 A1 | 5/2014 | Hendler et al. | |
| 2015/0133811 A1 | 5/2015 | Suzuki et al. | |
| 2015/0238104 A1 | 8/2015 | Tass | |
| 2015/0272461 A1 | 10/2015 | Morimoto et al. | |
| 2015/0305686 A1* | 10/2015 | Coleman | A61B 5/291 600/301 |
| 2016/0120436 A1 | 5/2016 | Silberstein | |
| 2016/0338608 A1 | 11/2016 | Nagasaka et al. | |
| 2017/0046498 A1* | 2/2017 | Reicher | G16H 50/50 |
| 2017/0095199 A1 | 4/2017 | Kranck | |
| 2018/0092567 A1 | 4/2018 | Nishimoto et al. | |
| 2020/0037911 A1* | 2/2020 | Hasegawa | G09B 21/00 |

FOREIGN PATENT DOCUMENTS

| | | |
|---|---|---|
| CN | 102946797 A | 2/2013 |
| CN | 104379052 A | 2/2015 |
| CN | 105163659 A | 12/2015 |
| CN | 105534534 A | 5/2016 |
| CN | 105989231 A | 10/2016 |
| CN | 106725302 A | 5/2017 |
| CN | 107427250 A | 12/2017 |
| EP | 3 064 130 A1 | 9/2016 |
| FR | 3 039 773 A1 | 2/2017 |
| JP | 2000-197619 A | 7/2000 |
| JP | 2001-037733 | 2/2001 |
| JP | 2002-253531 | 9/2002 |
| JP | 2003-159253 A | 6/2003 |
| JP | 2006-026065 | 2/2006 |
| JP | 2006-026066 | 2/2006 |
| JP | 2007-017248 | 1/2007 |
| JP | 2007-020594 | 2/2007 |
| JP | 2007-054138 A | 3/2007 |
| JP | 2008-517636 | 5/2008 |
| JP | 2008-194453 | 8/2008 |
| JP | 2008-289572 | 12/2008 |
| JP | 2010-022775 A | 2/2010 |
| JP | 2010-269087 | 12/2010 |
| JP | 2011-083433 | 4/2011 |
| JP | 2011-245202 | 12/2011 |
| JP | 2012-024390 A | 2/2012 |
| JP | 2012-081000 | 4/2012 |
| JP | 2012-239788 | 12/2012 |
| JP | 2013-128741 | 7/2013 |
| JP | 2015-066043 | 4/2015 |
| JP | 2016-047239 A | 4/2016 |
| JP | 2016-147089 A | 8/2016 |
| JP | 2016-195716 A | 11/2016 |
| JP | 2017-099450 | 6/2017 |
| JP | 2017-521129 | 8/2017 |
| WO | WO2006/009771 A1 | 1/2006 |
| WO | WO2006/026548 A1 | 3/2006 |
| WO | 2013/123112 A1 | 8/2013 |
| WO | 2014/053244 A1 | 4/2014 |
| WO | 2015/044851 A2 | 4/2015 |
| WO | WO2015/191628 A1 | 12/2015 |
| WO | 2016/207247 A1 | 12/2016 |
| WO | 2017/021662 A1 | 2/2017 |
| WO | 2017/024845 A1 | 2/2017 |
| WO | 2017/119638 A1 | 7/2017 |
| WO | WO 2017/185109 A1 | 11/2017 |

OTHER PUBLICATIONS

Extended European Search Report dated Apr. 16, 2019 in the corresponding European Application No. 18199573.9 9 pages.
U.S. Appl. No. 15/778,045, filed Nov. 8, 2016, Takafumi Ishibe, et al.
Combined Chinese Office Action and Search Report dated Apr. 30, 2021 in Chinese Patent Application No. 201811222265.0 (with English translation of Categories of Cited Documents), 13 pages.
Office Action dated Jun. 22, 2021 in Japanese Patent Application No. 2017-254677, 3 pages.
Chinese Office Action dated Nov. 15, 2021, in corresponding Chinese Patent Application No. 201811222265.0, 15 pp.
Office Action dated Apr. 28, 2022 in Chinese Patent Application No. 201811222265.0, 14 pages.
Office Action dated Sep. 23, 2022 in Chinese Patent Application No. 201811222265.0, 7 pages.

* cited by examiner

FIG. 4

| BRAIN FUNCTION | FIRST PAIR (STIMULATION-ANALYSIS) | SECOND PAIR (STIMULATION-ANALYSIS) | ... | N-TH PAIR (STIMULATION-ANALYSIS) | EXECUTION PROCEDURE |
|---|---|---|---|---|---|
| EPILEPTIC ACTIVITY | Pr1-Prs1 | Pr2-Prs2 | ... | — | FIRST PAIR, SECOND PAIR |
| COGNITIVE FUNCTION | Pr1-Prs3 | Pr3-Prs4 | ... | Prx-Prsy | SECOND PAIR, N-TH PAIR, ..., FIRST PAIR |
| .. | .. | .. | .. | .. | .. |
| .. | .. | .. | .. | .. | .. |

210

(1)

BIOLOGICAL FUNCTION MEASUREMENT AND ANALYSIS SYSTEM, BIOLOGICAL FUNCTION MEASUREMENT AND ANALYSIS METHOD, AND RECORDING MEDIUM STORING PROGRAM CODE

CROSS-REFERENCE TO RELATED APPLICATION

This patent application is based on and claims priority pursuant to 35 U.S.C. § 119(a) to Japanese Patent Application No. 2017-254677, filed on Dec. 28, 2017, in the Japan Patent Office, the entire disclosure of which is hereby incorporated by reference herein.

BACKGROUND

Technical Field

Embodiments of the present disclosure relate to a biological function measurement and analysis system, a biological function measurement and analysis method, and a recording medium storing program code causing a computer to execute a biological function measurement and analysis method.

Background Art

Systems are known in the art that acquire information about brain functions by giving stimulation to a subject according to the brain function, measuring the neural activity of the brain of the subject, and by analyzing the activity of the brain. As known in the art, some of such conventional systems enable a person who performs measurement to select the brain function for the measurement purposes and are provided with a program to be executed to change, for example, the duration for which stimulation is given according to the result of selection.

SUMMARY

Embodiments of the present disclosure described herein provide A biological function measurement and analysis system, a biological function measurement and analysis method, and a recording medium storing program code causing a computer to execute the biological function measurement and analysis method. The biological function measurement and analysis system includes an input acceptance unit configured to accept selection of a biological function to be measured, and a measurement and analysis procedure determining unit configured to access a memory in which measurement and analysis procedure data, indicating a combination of measurement and analysis of reaction of a live subject caused by stimulation on a biological-function-by-biological-function basis, is stored to specify measurement and analysis procedure data corresponding to the selected biological function. The biological function measurement and analysis method includes accepting the selection of biological function to be measured, accessing the memory in which measurement and analysis procedure data, indicating a combination of measurement and analysis of reaction of a live subject caused by stimulation on a biological-function-by-biological-function basis, is stored, and specifying the measurement and analysis procedure data corresponding to the selected biological function.

BRIEF DESCRIPTION OF THE DRAWINGS

A more complete appreciation of exemplary embodiments and the many attendant advantages thereof will be readily obtained as the same becomes better understood by reference to the following detailed description when considered in connection with the accompanying drawings.

FIG. 4 is a diagram illustrating a procedure database according to the first embodiment of the present disclosure.

Figure 1:
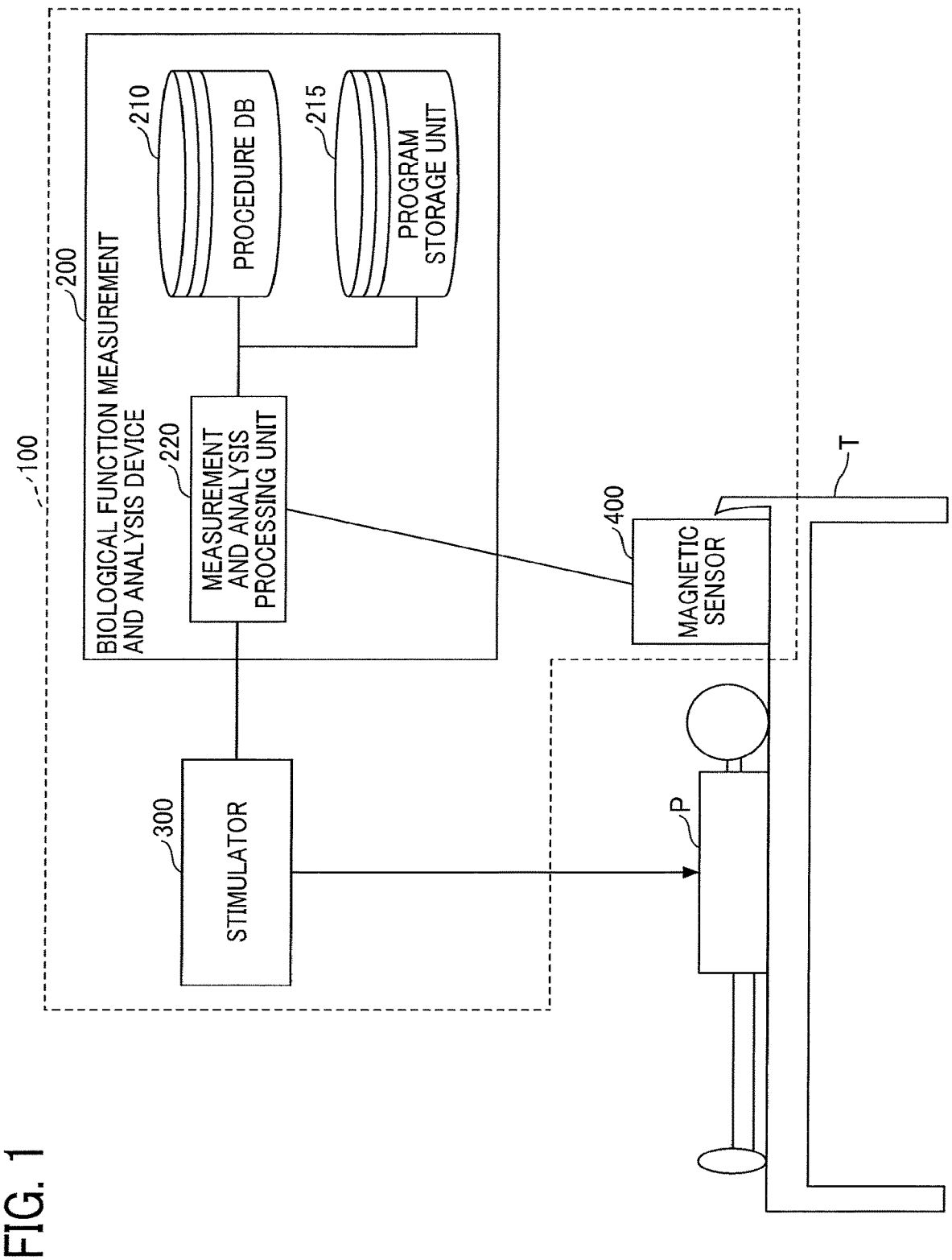
FIG. 1 is a diagram illustrating a system configuration of a biological function measurement and analysis system according to a first embodiment of the present disclosure.

The accompanying drawings are intended to depict exemplary embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments shown in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

In the following description, illustrative embodiments will be described with reference to acts and symbolic representations of operations (e.g., in the form of flowcharts) that may be implemented as program modules or functional processes including routines, programs, objects, components, data structures, etc., that perform particular tasks or implement particular abstract data types and may be implemented using existing hardware at existing network elements or control nodes. Such existing hardware may include one or more central processing units (CPUs), digital signal processors (DSPs), application-specific-integrated-circuits (ASICs), field programmable gate arrays (FPGAs), computers or the like. These terms in general may be collectively referred to as processors.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

First Embodiment

A first embodiment of the present disclosure is described below with reference to the accompanying drawings.

FIG. 1 is a diagram illustrating a system configuration of a biological function measurement and analysis system 100 according to the first embodiment of the present disclosure.

The biological function measurement and analysis system 100 according to the present embodiment includes a biological function measurement and analysis device 200, a stimulator 300, and a magnetic sensor 400.

In the biological function measurement and analysis system 100 according to the present embodiment, the stimulator 300 gives stimulation to a subject P to induce the neural activity of the brain, and the magnetic sensor 400 detects the magnetic field that is emitted from the neural activity. The magnetic sensor 400 outputs the detection results to the biological function measurement and analysis device 200. Note that the signals output from the magnetic sensor 400 to the biological function measurement and analysis device 200 may be referred to as sensor output signals in the following description.

The biological function measurement and analysis device 200 obtains and analyzes the sensor output signals output from the magnetic sensor 400, and outputs the results of the analysis (measurement results) as the information about the brain function (biological function).

The biological function measurement and analysis device 200 according to the present embodiment includes a procedure database (DB) 210, a program storage unit 215, and a measurement and analysis processing unit 220.

The procedure database 210 according to the present embodiment stores measurement and analysis procedure data where pairs of programs in which a stimulation program executed to instruct the stimulator 300 to generate stimulation and an analytical program used to analyze the sensor output signals corresponding to the stimulation are associated with each other are combined on a brain-function-by-brain-function basis. The measurement and analysis procedure data will be described later in detail.

The program storage unit 215 according to the present embodiment stores the entity of stimulation programs and analytical programs.

The measurement and analysis processing unit 220 according to the present embodiment accepts the selection of the function of the brain to be measured, and accesses the procedure DB 210 to specify the measurement and analysis procedure data that correspond to the selected function. Then, the measurement and analysis processing unit 220 instructs the stimulator 300 to generate stimulation according to the stimulation programs and the analytical programs indicated by the specified measurement and analysis procedure data, and analyzes the sensor output signals detected by the magnetic sensor 400 in response to the generated stimulation. Then, the measurement and analysis processing unit 220 outputs the results of analysis as the measurement results.

As described above, according to the present embodiment, the measurement and analysis procedure data is specified according to the selected brain function. Due to this configuration, measurement can be performed in accordance with the procedure that is determined in advance on a function-by-function basis. Accordingly, with the present embodiment, the measurement procedure does not vary depending on the person who performs measurement, and the measurement results can objectively be compared with each other.

The biological function measurement and analysis device 200 according to the present embodiment is further described below.

Figure 2:
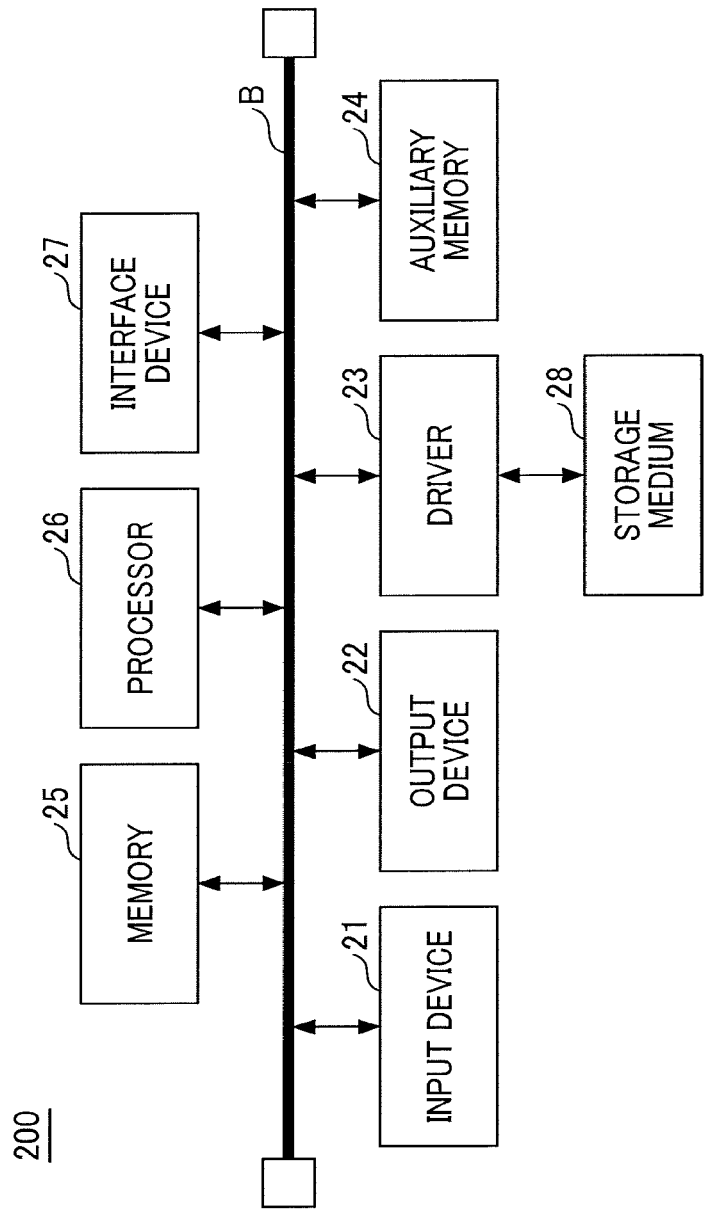
FIG. 2 is a diagram illustrating a hardware configuration of a biological function measurement and analysis device according to the first embodiment of the present disclosure.

FIG. 2 is a diagram illustrating a hardware configuration of the biological function measurement and analysis device 200 according to the first embodiment of the present disclosure.

The biological function measurement and analysis device 200 according to the present embodiment is an information processing device including an input device 21, an output device 22, a driver 23, an auxiliary memory 24, a memory 25, a processor 26, and an interface device 27, and these elements are interconnected through a bus B.

The input device 21 is a device through which various kinds of data are input, and is implemented by, for example, an input device such as a keyboard and a pointing device. The output device 22 is a device through which various kinds of data are output, and is implemented by, for example, a display interface. The interface device 27 includes, for example, a local area network (LAN) card, and is used to connect to the network.

A biological function measurement and analysis program is at least some of various programs for controlling the biological function measurement and analysis device 200. For example, the biological function measurement and analysis program may be provided by distributing the storage medium 28, or may be downloaded from the network. The storage medium 28 in which the biological function measurement and analysis program is stored may be implemented by various types of storage medium including a storage medium such as a compact disc read-only memory (CD-ROM), a flexible disk, or a magneto-optical disk that optically, electrically or magnetically records the data, and a semiconductor memory such as a read only memory (ROM) or a flash memory that electrically records the data.

For example, once the storage medium 28 in which the biological function measurement and analysis program is stored is connected to the driver 23, the biological function measurement and analysis program is installed onto the auxiliary memory 24 as extracted from the storage medium 28 through the driver 23. The biological function measurement and analysis program that is downloaded from the network is installed onto the auxiliary memory 24 through the interface device 27.

The auxiliary memory 24 stores the installed biological function measurement and analysis program, and further stores, for example, files or data as necessary. When the biological function measurement and analysis device 200 is turned on, the memory 25 extracts and stores the biological function measurement and analysis program from the auxiliary memory 24. Then, the processor 26 such as a central processing unit (CPU) implements various kinds of processes as will be described later in detail in accordance with the biological function measurement and analysis program stored in the memory 25.

The stimulator 300 according to the present embodiment is controlled by the biological function measurement and analysis device 200. More specifically, the stimulator 300 generates and outputs stimulation to be given to a subject P in accordance with the stimulation program executed by the biological function measurement and analysis device 200. Moreover, the stimulator 300 monitors, for example, the signals of magnetic field radiated from the subject P in accordance with the stimulation program executed by the biological function measurement and analysis device 200.

For example, the stimulator 300 according to the present embodiment may be an electrode disposed on a belt. In such cases, for example, the stimulator 300 is attached to an arm of the subject P, and an electrical signal or a mechanical signal is given to the subject P as a stimulus.

For example, the stimulator 300 according to the present embodiment may be a display interface or an audio output unit. In such a configuration, for example, the stimulator 300 gives the picture displayed on the stimulator 300 or the voice output from the stimulator 300 to the subject P as a stimulus. As described above, the stimulator 300 according to the present embodiment can give various kinds of stimulation defined by the measurement procedure to the subject P.

As described above, in the biological function measurement and analysis system 100 according to the present embodiment, the magnetic sensor 400 detects the signals radiated from the neural activity of the brain of the subject P. However, no limitation is intended thereby. The biological function measurement and analysis system 100 according to the present embodiment is satisfactory as long as it is provided with a sensor that detects the signals radiated from the neural activity of the brain, and it is desired that the sensor be minimally invasive such that the biological function of a subject will accurately be measured. It is even more desirable if the sensor is non-invasive. Apart from a magnetic sensor, for example, such a sensor may adopt brainwave topography or optical topography. The sensor according to the present embodiment may include a plurality of kinds of sensors. However, in such cases, it is desired to be configured such that the operation of one sensor does not affect the measurement performed by the other sensors. In particular, when a magnetic sensor is used as one of the sensors, the signals radiated from the live subject can be obtained even when the magnetic sensor does not contact a live subject. For this reason, the state of attachment of a magnetic sensor does not affect the measurement results, and it is considered that a magnetic sensor is desirable in the present embodiment. However, no limitation is intended thereby, and the sensors used the present embodiment may include different kinds of sensor.

Next, functions of the biological function measurement and analysis device 200 according to the present embodiment are described with reference to FIG. 3.

Figure 3:
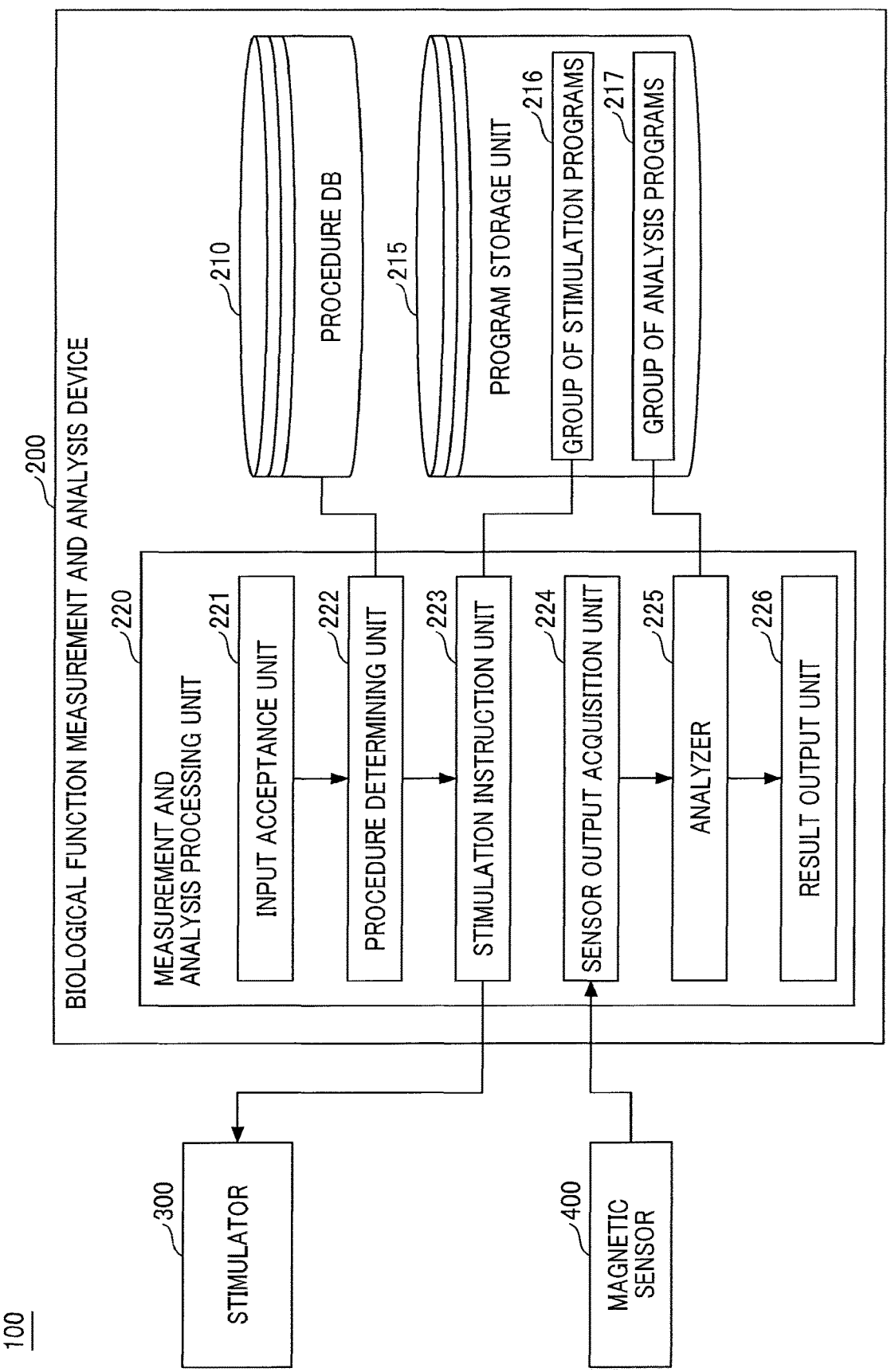
FIG. 3 is a diagram illustrating a functional configuration of a biological function measurement and analysis device according to the first embodiment of the present disclosure.

FIG. 3 is a diagram illustrating functions of the biological function measurement and analysis device 200 according to the first embodiment.

The biological function measurement and analysis device 200 according to the present embodiment includes a procedure database (DB) 210, a program storage unit 215, and a measurement and analysis processing unit 220.

For example, the procedure DB 210 and the program storage unit 215 is implemented by the auxiliary memory 24 or the memory 25 of the biological function measurement and analysis device 200. For example, the measurement and analysis processing unit 220 according to the present embodiment is implemented by the processor 26 extracting and executing the biological function measurement and analysis program stored in the auxiliary memory 24 or the memory 25.

The program storage unit 215 according to the present embodiment stores a group of stimulation programs 216 that instructs the stimulator 300 to generate stimulation and a group of analytical programs 217 that analyzes the sensor output signal output from the magnetic sensor 400. The group of stimulation programs 216 and the group of analytical programs 217 may be stored in the program storage unit 215 in advance. Alternatively, the biological function measurement and analysis device 200 may communicate with an external device to download the group of stimulation programs 216 and the group of analytical programs 217 therefrom.

The measurement and analysis processing unit 220 includes an input acceptance unit 221, a procedure determining unit 222, a stimulation instruction unit 223, a sensor output acquisition unit 224, an analyzer 225, a result output unit 226.

The input acceptance unit 221 accepts various kinds of information input to the biological function measurement and analysis device 200. In particular, for example, the input acceptance unit 221 accepts the operation of selecting the brain function (biological function) to be measured by the biological function measurement and analysis system 100.

Once the operation of selecting the brain function is accepted by the input acceptance unit 221, the procedure determining unit 222 refers to the procedure DB 210 to specify the measurement and analysis procedure data that correspond to the selected function. In other words, the procedure determining unit 222 determines the measurement procedure according to the selected brain function.

The stimulation instruction unit 223 instructs the stimulator 300 to generate stimulation based on the stimulation program included in the measurement and analysis procedure data determined by the procedure determining unit 222. In other words, the stimulation instruction unit 223 extracts the stimulation program included in the determined measurement and analysis procedure data from the group of stimulation programs 216 stored in the program storage unit 215, and executes the extracted stimulation program in the order defined in the measurement and analysis procedure data.

The sensor output acquisition unit 224 obtains the sensor output signal output from the magnetic sensor 400 while the stimulation program is being executed. More specifically, the sensor output acquisition unit 224 is connected to, for example, an output terminal of the magnetic sensor 400, and obtains the sensor output signal output from such an output terminal.

The analyzer 225 analyzes the sensor output signal based on the analytical program associated with the stimulation program extracted by the stimulation instruction unit 223, from among the analytic programs included in the measurement and analysis procedure data determined by the procedure determining unit 222. In other words, the analyzer 225 extracts the analytical program associated with the stimulation program determined to be used for generating stimulation, from the group of analytical programs 217 stored in the program storage unit 215, and executes the extracted analytical program.

The result output unit 226 output the analytical results obtained by the analyzer 225 as the results of the measurement of the brain function. In other words, the result output unit 226 output the results of the execution of the analytical program as the results of the measurement of the brain function.

The procedure DB 210 according to the present embodiment is described below with reference to FIG. 4.

FIG. 4 is a diagram illustrating the procedure DB 210 according to the first embodiment.

The procedure database 210 according to the present embodiment contains items of data including the brain functions, the first pair, the second pair, . . . , and N-th pair, and the execution procedures.

The item "brain function" is associated with the other items in the procedure database 210. The measurement and analysis procedure data according to the present embodiment includes values for the item "brain function" and values for the other items.

The value of the item "brain function" indicates the function of the brain to be measured. The values for the items "first pair" to "N-th pair" indicate the association between the stimulation programs and the analytical programs. The values for the item "execution procedure" indicate the order in which the items "first pair" to "N-th pair" are executed.

In other words, the measurement and analysis procedure data according to the present embodiment includes the data indicating the association between the stimulation programs and the analytical programs. In other words, the measurement and analysis procedure data is the data indicating the combination of stimulation and analysis as a measurement procedure.

For example, in view of the example of FIG. 4, it is understood that the stimulation programs and the analytical programs are executed in the order from the first pair to the second pair when the "epileptic activity" of the brain is to be measured. In the example of FIG. 4 where the epileptic activity is to be measured, a stimulation program Pr1 and an analytical program Prs1 are associated with each other in the first pair, and a stimulation program Pr2 and an analytical program Prs2 are associated with each other in the second pair.

Accordingly, in the example of FIG. 4, the "epileptic activity" of a brain is measured in the order from execution of the stimulation program Pr1 to execution of the analytical program Prs1, then to execution of the stimulation program Pr2, and then to execution of the analytical program Prs2.

In a similar manner to the above, in view of the example of FIG. 4, it is understood that the stimulation programs and the analytical programs are executed in the order from the second pair to N-th pair, then to some pairs between the second pair and the N-th pair, and then to the first pair when the "cognitive function" of the brain is to be measured. In the example of FIG. 4 where the cognitive function is to be measured, the stimulation program Pr1 and an analytical program Prs3 are associated with each other in the first pair, and a stimulation program Pr3 and an analytical program Prs4 are associated with each other in the second pair. Moreover, a stimulation program Prx and an analytical program Prsy are associated with each other in the N-th pair.

Accordingly, in the example of FIG. 4, the "cognitive function" of a brain is measured in the order from execution of the stimulation program Pr3 to execution of the analytical program Prs5, then to execution of the stimulation program Prx, then to execution of the analytical program Prsy, then to some pairs between the second pair and the N-th pair, then to execution of the execution of the stimulation program Pr1, and then to execution of the analytical program Prs3.

In the example as illustrated in FIG. 4, it is assumed that one analytical program is associated with one stimulation program. However, no limitation is intended thereby. In the present embodiment, a plurality of analytical programs may be associated with one stimulation program, or one analytical program may be associated with a plurality of stimulation programs.

In the example depicted in FIG. 4, only the order in which the pairs are executed is specified as the values for the item "execution procedure." However, no limitation is intended thereby. For example, in the procedure DB 210, a value indicating an interval (a certain length of time) between a timing at which a certain pair (procedure) is executed and a timing at which the next pair (next procedure) is executed may be included in the values for the items "execution procedure."

More specifically, for example, when the value for the item "brain function" is the "cognitive function" in the present embodiment, the length of time indicating the intervals between pairs may be included in the values for the items "execution procedure."

In such a case, for example, the stimulation instruction unit 223 gives instructions to the stimulator 300 based on the stimulation program Pr2 included in the second pair after the length of time indicating the intervals has passed after instructing the stimulator 300 to generate and output stimulation based on the stimulation program Pr1 included in the first pair.

The timing at which the measurement of time is to start, as indicated by the intervals, may be the timing at which the stimulation instruction unit 223 has given instructions based on the stimulation program Pr1 included in the first pair. Alternatively, the timing at which the measurement of time is to start may be the timing at which the execution of the analytical program Prs1 included in the first pair has been completed.

The measurement of "epileptic activity," "cognitive function," or the like includes various kinds of measurement related to the low-order to high-order brain functions such as the auditory sense, the visual sense, the sense of touch, the gustatory sense, the olfactory sense, the somatic sensation, the movement, the language, the memory, the attention, the behavior, and the sociability.

There are some cases in which the state of the brain of a subject P has been changed immediately after the measurement of high-order brain functions such as the language, the memory, the attention, the behavior, and the sociability was performed. In order to deal with such a situation, in the present embodiment, an interval is placed between stimuli in order to bring the state of the brain of the subject P back to normal. When stimulation that simultaneously induces a plurality of low-order brain functions is used to measure the low-order brain functions such as the auditory sense, the visual sense, the sense of touch, the gustatory sense, the olfactory sense, the somatic sensation, and the movement, an interval may similarly be placed between stimuli in order to bring the state of the brain of the subject P back to normal.

For example, when the stimulation given to the subject P include moving images with sound, such stimulation is related to the auditory sense and the visual sense. Accordingly, it is desired that the length of time indicating the intervals between the pair including the stimulation program that gives moving images including sound and the next pair be included as the values for the item "execution procedure."

The stimulation that is given to a subject P by the stimulation programs according to the present embodiment is further described below.

In the biological function measurement and analysis system 100 according to the present embodiment, the stimulation that is given to the subject P includes various patterns of stimulation. Such various patterns of stimulation are implemented by executing pairs of programs including various patterns of stimulation programs in various kinds of procedure.

More specifically, for example, after the results of giving certain stimulation (first stimulation) to the subject P are analyzed, analysis may be performed upon giving stimulation (second stimulation) different from the above certain stimulation to the subject P. Further, after the results of giving the second stimulation to the subject P are analyzed, analysis may be performed again upon giving the above certain stimulation (first stimulation) to the subject.

In such a configuration, the execution procedure may indicate the order in which pairs of programs are executed as follows. The second pair including a stimulation program used to generate the second stimulation is to be executed subsequent to the first pair including a stimulation program used to generate the first stimulation. Then, the first group is to be executed again.

In the present embodiment, stimulation is given to the subject P as described above. Accordingly, for example, the analytical results obtained in response to the first stimulation given to the subject P for the first time can be compared with the analytical results obtained in response to the first stimulation given to the subject P for the second time, to estimate the effect exerted on the subject P by the second stimulation.

In the present embodiment, for example, a pair of programs including a stimulation program used to generate the same stimulation as above to be given to the subject P for length of time sufficiently longer than the above certain length of time may be used in combination subsequent to a pair of programs including a stimulation program used to generate stimulation to be given to the subject P for certain length of time.

In such a case, for example, the stimulation that is given to the subject P for certain length of time may be considered to be a test measurement of the function, and a pair of programs including a stimulation program used to generate stimulation to be given to the subject P for length of time sufficiently longer than the above certain length of time may be executed depending on the results of analysis performed by the analytical program associated with the stimulation program used to give the above stimulation.

In the present embodiment, the stimulation that is given to the subject P for certain length of time is referred to as a unit of stimulation. The above length of time sufficiently longer than a certain length of time may be an interval about ten times longer than the certain length of time.

Further, in the present embodiment, a pair of programs in which a stimulation program and an analytical program are associated with each other may include a pair of programs that includes a stimulation program that does not give any stimulation to the subject P. Due to such a configuration, the so-called resting state of a brain can be measured. As an analytical program that analyzes the resting state of a brain, for example, a beamformer method in which the number of the active regions of the brain is not limited may be adopted. Alternatively, a pair of programs may include a functionality connection analysis that evaluates the association among those multiple active regions of the brain.

The stimulation program in the above case controls the stimulator 300 to terminate the generation and output of stimulation for certain length of time. In so doing, the stimulation program may control the stimulator 300 to monitor (measure) the signals radiated from the subject P. The signals that are radiated from the subject P are, for example, the brain waves of the subject P.

In the execution procedure including such a stimulation program used to terminate the stimulation output and monitor the subject P, the pair of programs that includes such a stimulation program may be executed in the first half of the execution procedure. For example, the pair of programs that includes such a stimulation program may be the first pair to be executed.

In the present embodiment, a pair of programs including a stimulation program used to terminate the stimulation output and monitor the subject P is executed in the first half of the execution procedure. For example, such a pair of programs is the first pair to be executed. Due to this configuration, the state of the neural activity of the brain when the subject P is in a resting state can preliminarily be measured before any stimulation is given to the subject.

If the state of the neural activity of the brain of the subject P is preliminarily measured in a resting state before any stimulation is given to the subject P, the preliminarily-measured state of neural activity can be compared with the state of the neural activity of the brain of the subject P after some stimulation has been given to the subject P in an analytical program. Due to this configuration, analysis can be performed in view of the effect induced by the stimulation. As a result, function measurement can be performed where, for example, the parameter or flow of execution of the stimulation program is adjusted to achieve constant conditions of a subject.

For example, whether or not the subject P is in a sleep state can be determined by monitoring the brain waves of the subject P in a resting state. Due to this configuration, when a function of the brain of the subject P is to be measured while the subject P is sleeping, for example, the biological function measurement and analysis device 200 can be configured to give stimulation to the brain of the subject P after it is detected that the subject P is in a sleep state in view of the results of the analysis of sensor output signals. Alternatively, when a function of the brain of the subject P is to be measured while the subject P is awake, for example, the biological function measurement and analysis device 200 can be configured to give stimulation for measuring the biological function after stimulation that could lead to awakening is given to the subject P and it is then detected that the subject P is in an awakening state in view of the results of the analysis of sensor output signals.

The processes of the biological function measurement and analysis device 200 according to the present embodiment are described below with reference to FIG. 5 and FIG. 6.

Figure 5:
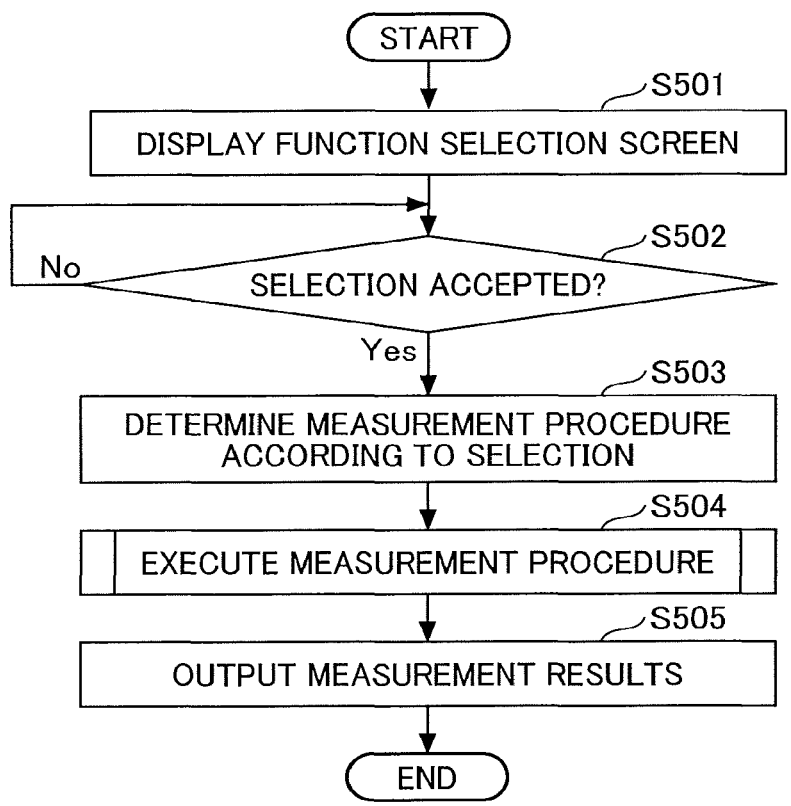
FIG. 5 is a first flowchart of processes of a biological function measurement and analysis device according to the first embodiment.

FIG. 5 is a first flowchart of the processes of the biological function measurement and analysis device 200 according to the first embodiment.

For example, the biological function measurement and analysis device 200 according to the present embodiment uses the input acceptance unit 221 of the biological function measurement and analysis device 200 to control the display of the biological function measurement and analysis device 200 to display a selection screen on which the function of the brain to be measured can be selected (step S501). It is not necessary for the biological function measurement and analysis device 200 to be provided with the display on which the selection screen is displayed, but the display on which the selection screen is displayed may be, for example, a terminal device that communicates with the biological function measurement and analysis device 200. The selection screen will be described later in detail.

Subsequently, the measurement and analysis processing unit 220 determines whether or not the input acceptance unit 221 has accepted the selection of the function of the brain to be measured (step S502). When no selection is accepted in the step S502, the measurement and analysis processing unit 220 is on standby waiting until a selection is accepted.

Once the input acceptance unit 221 has accepted a selection in the step S502, the measurement and analysis processing unit 220 uses the procedure determining unit 222 to access the procedure DB 210, and determines the measurement procedure that correspond to the selected brain function (step S503).

In other words, the procedure determining unit 222 accesses the procedure DB 210 to specify the measurement and analysis procedure data that includes the selected brain function.

Subsequently, the measurement and analysis processing unit 220 executes the measurement procedure determined by the procedure determining unit 222 (step S504). The processes in the step S504 will be described later in detail.

Subsequently, the measurement and analysis processing unit 220 uses the result output unit 226 to output the measurement results (step S505), and terminates the processes.

The processes of executing a measurement procedure by the measurement and analysis processing unit 220 are described below with reference to FIG. 6.

Figure 6:
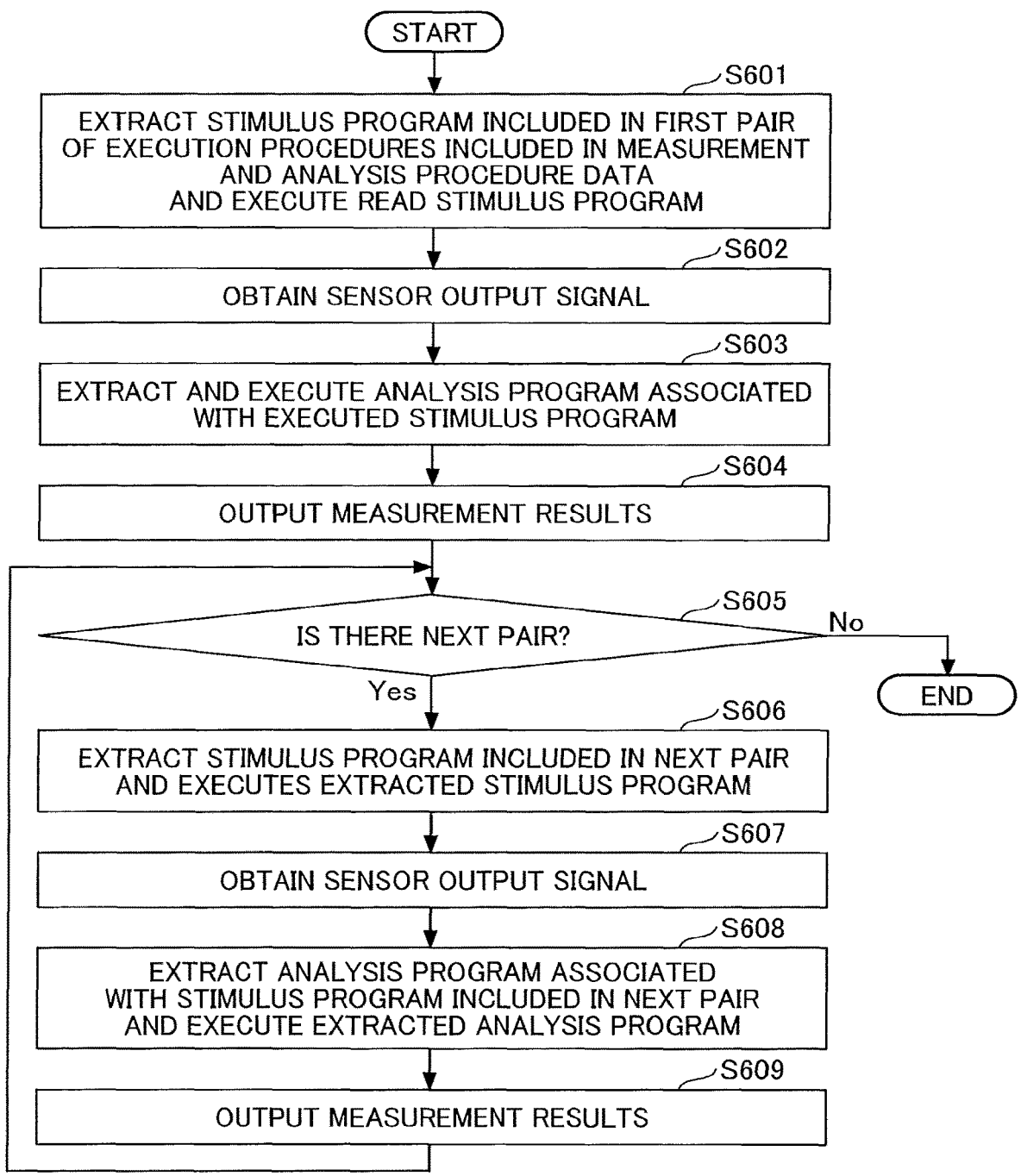
FIG. 6 is a second flowchart of the processes of a measurement and analysis processing unit according to the first embodiment.

FIG. 6 is a second flowchart of the processes of the measurement and analysis processing unit 220 according to the first embodiment. In FIG. 6, the processes in the step S504 of FIG. 5 are depicted in detail.

Once the measurement and analysis procedure data is specified, the measurement and analysis processing unit 220 according to the present embodiment uses the stimulation instruction unit 223 to extract from the program storage unit 215 the stimulation program included in the first pair of the pairs of execution procedures included in the measurement and analysis procedure data, and execute the extracted stimulation program (step S601). In other words, the stimulation instruction unit 223 extracts a stimulation program and executes the extracted stimulation program to control the stimulator 300 based on the executed stimulation program.

For example, when the stimulation program in the above case is to give a unit of stimulation, the stimulation instruction unit 223 controls the stimulator 300 to output a unit of stimulation to the subject P.

Alternatively, when the stimulation program in the above case is to terminate the output of stimulation, the stimulation instruction unit 223 controls the stimulator 300 to terminate the output of stimulation and monitor the signals radiated from the subject P.

Subsequently, the measurement and analysis processing unit 220 causes the sensor output acquisition unit 224 to acquire the sensor output signal output from the magnetic sensor 400 (step S602). Subsequently, the measurement and analysis processing unit 220 uses the analyzer 225 to extract the analytical program associated with the stimulation program executed in the step S601 from the program storage unit 215, and executes the extracted analytical program (step S603).

Subsequently, the measurement and analysis processing unit 220 uses the result output unit 226 to output the result of executing the analytical program as the measurement results (step S604).

Subsequently, the measurement and analysis processing unit 220 determines whether there is a next pair in the execution procedure included in the measurement and analysis procedure data (step S605). When there is not a next process (pair) in the step S605, the measurement and analysis processing unit 220 terminates the process.

When there is a next pair (process) in the step S605, the measurement and analysis processing unit 220 uses the stimulation instruction unit 223 to extract the stimulation program included in the next pair from the program storage unit 215 and execute the extracted stimulation program (step S606).

Subsequently, the measurement and analysis processing unit 220 uses the sensor output acquisition unit 224 to obtain the sensor output signal output from the magnetic sensor 400 (step S607). Subsequently, the measurement and analysis processing unit 220 uses the analyzer 225 to extract the analytical program included in the next pair corresponding to the stimulation program executed in the step S606 and execute the extracted analytical program (step S608).

Subsequently, the measurement and analysis processing unit 220 uses the result output unit 226 to output the result of executing the analytical program as the measurement results (step S609) and return to the step S605.

As described above, in the present embodiment, the measurement procedure that is defined in the measurement and analysis procedure data is executed. In the example as illustrated in FIG. 6, the results of the execution of the analytical program are output as the results of measurement every time an analytical program is executed. However, no limitation is intended thereby. In the present embodiment, the results of the execution of the analytical program may temporarily be stored, and the results of measurement may collectively be output after all the pairs included in the measurement procedure have been executed.

In the example depicted in FIG. 6, pairs of programs are executed in chronological order. However, no limitation is intended thereby. In the present embodiment, the analytical program included in a certain pair of programs and the stimulation program included in the next pair of programs may be performed in parallel.

In the example as illustrated in FIG. 6, it is assumed that one analytical program is executed in response to one stimulation program. However, no limitation is intended thereby. In the present embodiment, for example, a plurality of analytical programs that implement a plurality of different analyzing methods may be performed in response to the sensor output signal obtained by executing one stimulation program. Such a plurality of analyzing methods include, for example, a dipole method and a beamformer method.

Next, a selection screen on which the brain function is to be selected, which is displayed by the biological function measurement and analysis device 200, is described with reference to FIG. 7.

Figure 7:
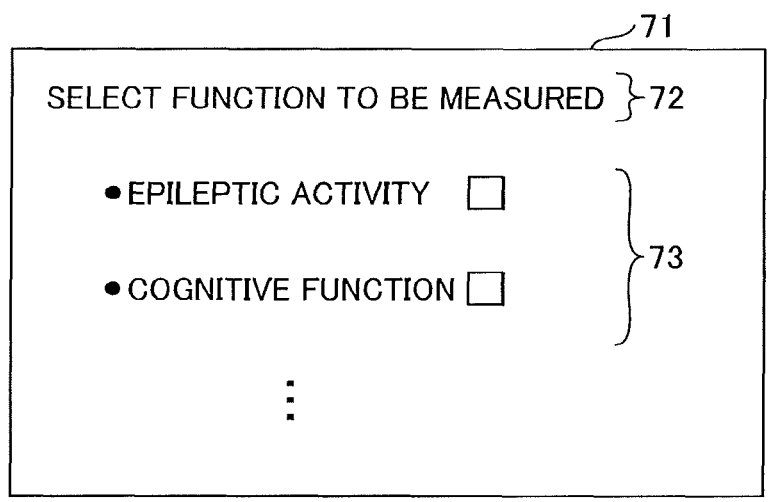
FIG. 7 is a diagram illustrating a selection screen according to the first embodiment of the present disclosure.

FIG. 7 is a diagram illustrating a panel of options to be selected according to the first embodiment.

On the selection screen 71 as illustrated in FIG. 7, a message 72 and a selection field 73 are displayed. The message 72 prompts a user to select the brain function to be measured.

The selection field 73 includes a list of brain functions and checkboxes to select the respective brain functions. In an alternative embodiment of the present disclosure, the selection screen may be a screen from which only one of the multiple options is to be selected. In such a configuration, the options may be, for example, "brain function of infants" and "brain function of elderly people" that a person who performs measurement can easily select. Due to such a configuration, the person who performs measurement can make an appropriate selection even if he or she does not have sufficient knowledge or skills. Accordingly, there is an advantageous effect that the results of measurement of the biological function measurement and analysis device according to the present embodiment can objectively and easily be compared with each other.

Moreover, options that are based on the objective attribute of a subject such as an age group or gender, results of various kinds of psychological tests, a result of image inspection that is different from the methods described in the present disclosure, or various kinds of inspection results of, for example, a blood test and an examination of cerebrospinal fluid (CSF) are desirable because the person who performs measurement can make a selection easily.

In the present embodiment, once the brain function to be measured is selected on the selection field 73, the input acceptance unit 221 accepts that selection, and the procedure determining unit 222 specifies the measurement and analysis procedure data associated with the selected brain function.

Accordingly, with the present embodiment, the person who performs measurement only has to select the brain function to be measured, and does not have to specify, for example, the order in which stimulation is given to the subject P or the order in which analysis is performed. In other words, with the present embodiment, the way stimulation is given or the procedure for analysis or the like does not vary depending on the person who performs measurement, and comparison between the measurement results can be done objectively.

Second Embodiment

A second embodiment of the present disclosure is described below with reference to the accompanying drawings. The second embodiment is different from the first embodiment in the respect that a parameter included in a stimulation program is changed depending on the results of analysis performed by an analytical program. Accordingly, in the descriptions of the second embodiment as given below, only the differences from the first embodiment will be described. Like reference signs are given to like elements in the second embodiment, and their detailed description is omitted.

Figure 8:
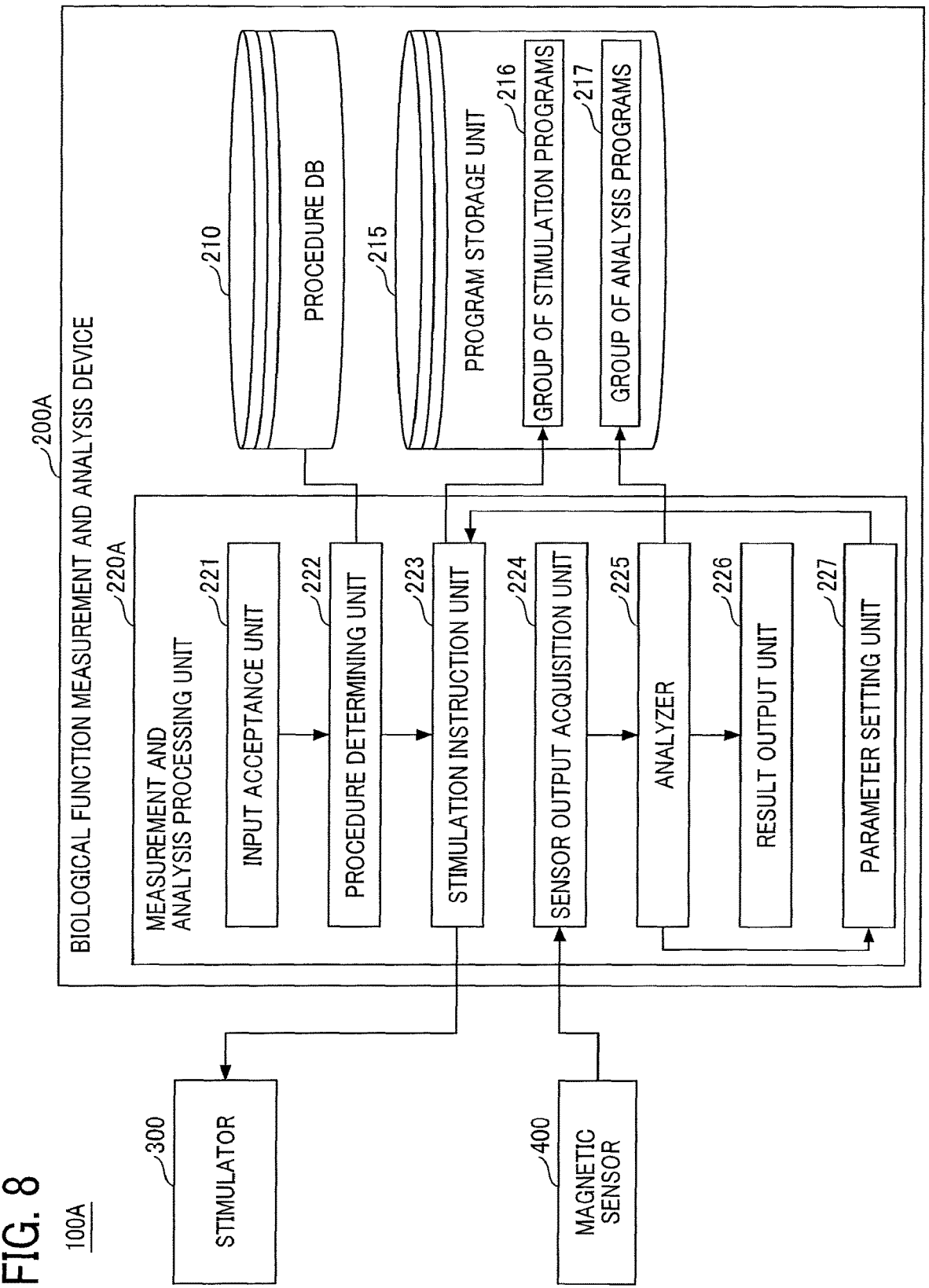
FIG. 8 is a diagram illustrating a functional configuration of a biological function measurement and analysis device according to a second embodiment.

FIG. 8 is a diagram illustrating a functional configuration of a biological function measurement and analysis device 100A according to the second embodiment. The biological function measurement and analysis system 100A according to the present embodiment includes a biological function measurement and analysis device 200A.

The biological function measurement and analysis device 200A includes the procedure DB 210, the program storage unit 215, and a measurement and analysis processing unit 220A.

The measurement and analysis processing unit 220A according to the present embodiment includes the input acceptance unit 221, the procedure determining unit 222, the stimulation instruction unit 223, the sensor output acquisition unit 224, the analyzer 225, the result output unit 226, and the parameter setting unit 227.

The parameter setting unit 227 according to the present embodiment changes the parameter of the next stimulation program to be executed according to the results of the execution of the analytical program by the analyzer 225. The parameters included in the stimulation program are, for example, the length of time during which stimulation is given and the intensity of the stimulation.

The parameter setting unit 227 according to the present embodiment has, for example, a predetermined threshold for the analytical results of the analyzer 225, and for example, when the value output as a result of executing an analytical program is equal to or greater than a predetermined threshold, the parameter of the next stimulation program to be executed may be changed. In the present embodiment, the stimulation generated by the next stimulation program to be executed is the same as the previously-generated stimulation, and only the parameters are different from each other. In other words, the type of stimulation caused by the next stimulation program to be executed (i.e., the stimulation program included in the second pair) is the same as the type of stimulation caused by the previously-executed stimulation program (i.e., the stimulation program included in the first pair), and only the parameters are different from each other.

For example, when the value output as a result of executing an analytical program is less than a predetermined threshold, the parameter setting unit 227 may increase the intensity of the stimulation or the length of time for which stimulation is given in the next stimulation program to be executed. When the brain function that is to respond to the stimulation composed of multiple trials (for example, equal to or more than one hundred trials) of the same stimulation is measured, some of those trials (for example, ten trials) may induce no significant response due to a lack of attention of a subject. In order to avoid such a situation, when the number of the trials that has induced a significant response does not reach a number of times required to measure the brain function as a result of executing an analytical program, the parameter may be edited to have a value (for example, twelve) such that the next stimulation program to be executed will give additional same stimulation and the number of the trials that induce a significant response becomes equal to or exceeds the number of times required to measure the brain function. For example, when the stimulation is an acoustic stimulus, it is effective to increase the sound pressure level (SPL) so as to be greater than an appropriate SPL (for example, to 5 decibels (dB)) in order to arouse an attention of the subject.

The operations of the biological function measurement and analysis device 200A according to the present embodiment are described below. The operations of the biological function measurement and analysis device 200A according to the present embodiment is different from the first embodiment only in the process of executing the measurement procedure (step S504 in FIG. 5).

Accordingly, only the execution of a measurement procedure in the second embodiment is described below with reference to FIG. 9.

Figure 9:
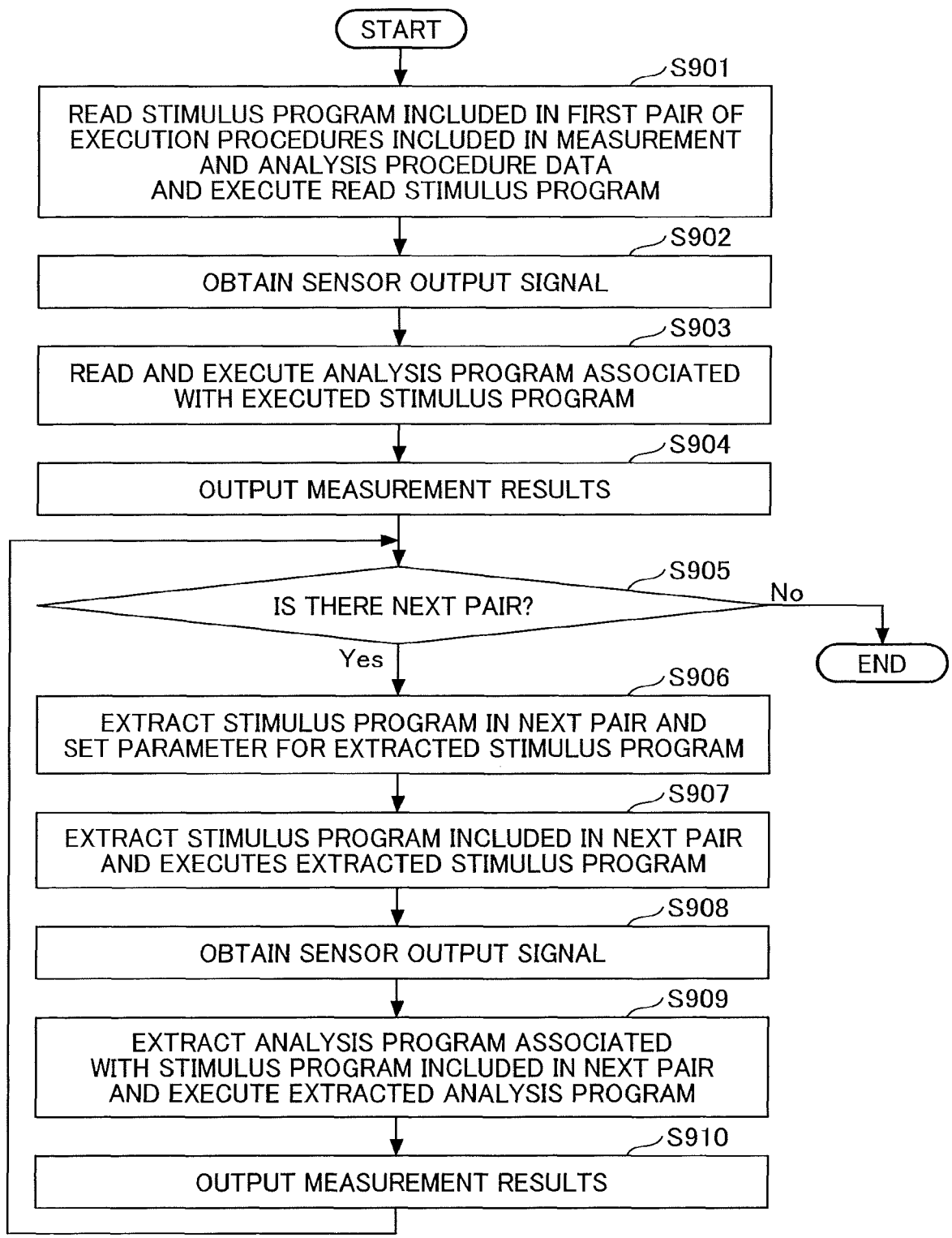
FIG. 9 is a flowchart of processes of a measurement and analysis processing unit according to the second embodiment.

FIG. 9 is a flowchart of the processes of the measurement and analysis processing unit 220A according to the second embodiment. More specifically, FIG. 9 depicts the processes of executing the measurement procedure determined by the procedure determining unit 222 of biological function measurement and analysis device 200A.

Since the processes in steps S901 to S905 of FIG. 9 are similar to the processes in the steps S601 to S605 of FIG. 6, the description of those processes is omitted.

When there is a next process (pair) in the step S905, the measurement and analysis processing unit 220A uses the parameter setting unit 227 to set a parameter for the stimulation program included in the next pair based on the results of the execution of the analytical program in the step S903 (step S906), and the process proceeds to a step S907.

Since the processes in steps S907 to S910 of FIG. 9 are similar to the processes in the steps S606 to S609 to of FIG. 6, the description of those processes is omitted.

As described above, with the present embodiment, the intensity or duration of the stimulation to be given to the subject P for the next time can be changed according to the result of giving certain stimulation to the subject P.

Third Embodiment

A third embodiment of the present disclosure is described below with reference to the accompanying drawings. The third embodiment is different from the first embodiment in the respect that the procedure DB 210, the program storage unit 215, the analyzer 225, and the result output unit 226 are provided for a device outside the biological function measurement and analysis device 200. Accordingly, in the descriptions of the third embodiment as given below, only the differences from the first embodiment will be described. Like reference signs are given to like elements in the second embodiment, and their detailed description is omitted.

Figure 10:
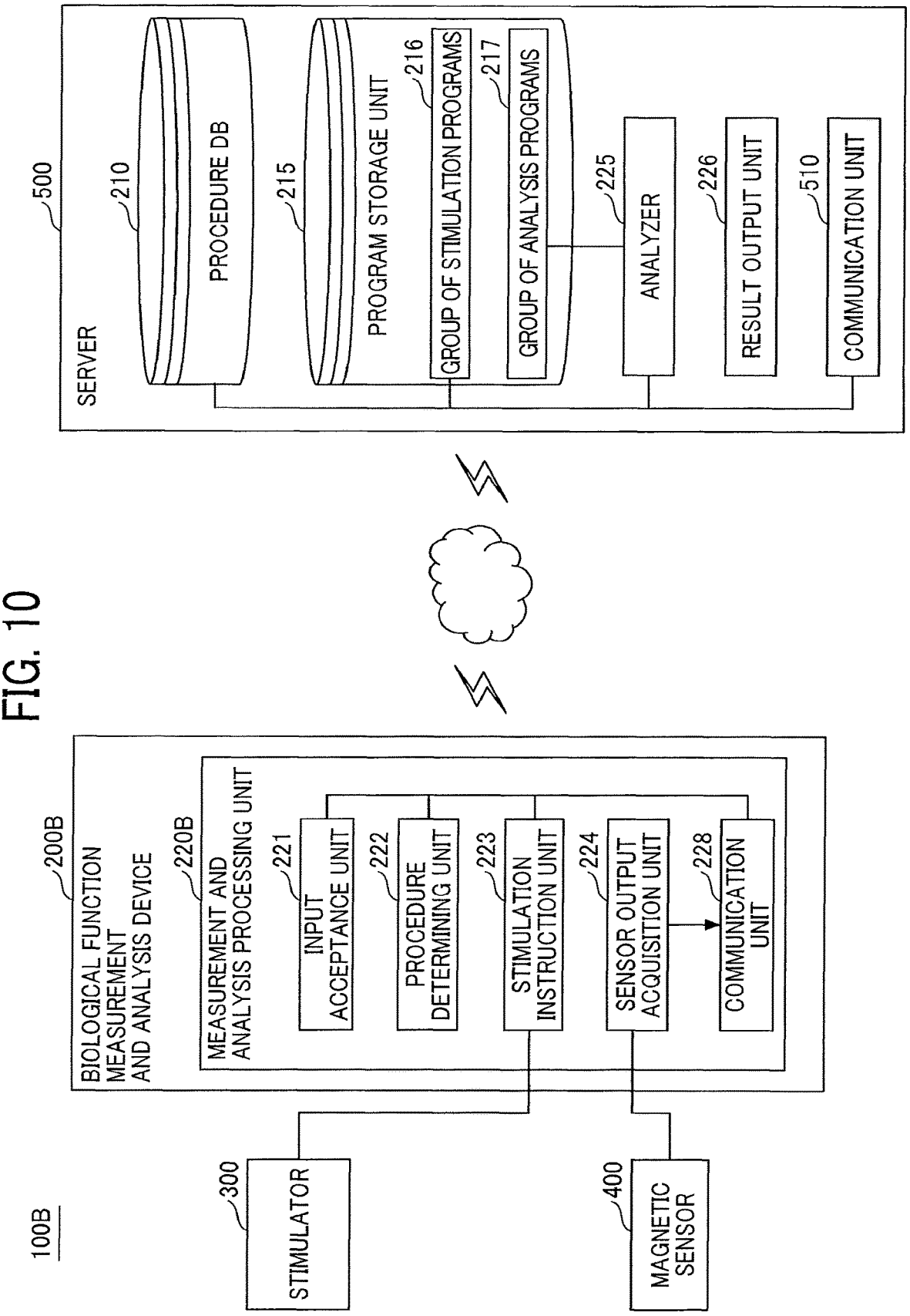
FIG. 10 is a diagram illustrating a biological function measurement and analysis system according to a third embodiment.

FIG. 10 is a diagram illustrating a biological function measurement and analysis system according to the third embodiment. The biological function measurement and analysis system 100B according to the present embodiment includes a biological function measurement and analysis device 200B, the stimulator 300, the magnetic sensor 400, and the server 500.

The biological function measurement and analysis device 200B according to the present embodiment includes a measurement and analysis processing unit 220B. The measurement and analysis processing unit 220B includes the input acceptance unit 221, the procedure determining unit 222, the stimulation instruction unit 223, a sensor output acquisition unit 224, a communication unit 228. The communication unit 228 communicates with an external device including the server 500.

The server 500 according to the present embodiment includes the procedure DB 210, the program storage unit 215, the analyzer 225, the result output unit 226, and a communication unit 510. The communication unit 510 communicates with an external device including the biological function measurement and analysis device 200B.

Once the selection of the function of the brain to be measured is accepted by the input acceptance unit 221, the biological function measurement and analysis device 200B according to the present embodiment uses the communication unit 228 to access the procedure DB 210 provided for the server 500, and uses the procedure determining unit 222 to specify the measurement and analysis procedure data. In so doing, the communication unit 228 may pass the specified measurement and analysis procedure data to the analyzer 225 of the server 500.

Once the measurement and analysis procedure data is specified, the biological function measurement and analysis device 200B according to the present embodiment accesses the server 500 through the communication unit 228 to read a stimulation program according to the measurement and analysis procedure data, and controls the stimulation instruction unit 223 to execute a stimulation program.

Then, once the stimulation program is executed by the stimulation instruction unit 223, the biological function measurement and analysis device 200B sends the data indicative of the executed stimulation program and a notification that the stimulation program has been executed to the server 500 through the communication unit 228.

Then, once the sensor output signal is obtained from the magnetic sensor 400 using the sensor output acquisition unit 224, the biological function measurement and analysis device 200B sends the sensor output signal to the server 500 through the communication unit 228.

In response to a notification that the stimulation program has been executed, the server 500 uses the analyzer 225 to execute the analytical program on the sensor output signal according to the measurement and analysis procedure data, and controls the result output unit 226 to output the measurement results.

As described above, according to the present embodiment, the analyzer 225 that performs analytical processing and the program storage unit 215 in which the group of stimulation programs 216 and the group of analytical programs 217 are stored are provided for the server 500. Due to this configuration, the storage of the memory or the load of processing, each of which is required in the biological function measurement and analysis device 200B, can be reduced.

Fourth Embodiment

A fourth embodiment of the present disclosure is described below with reference to FIG. 11. The fourth embodiment is different from the first embodiment in that a storage unit in which the group of analytical programs 217 is stored, the analyzer 225, and the result output unit 226 re arranged in an external device of the biological function measurement and analysis device 200. Accordingly, in the descriptions of the fourth embodiment as given below, only the differences from the first embodiment will be described. Like reference signs are given to like elements in the second embodiment, and their detailed description is omitted.

Figure 11:
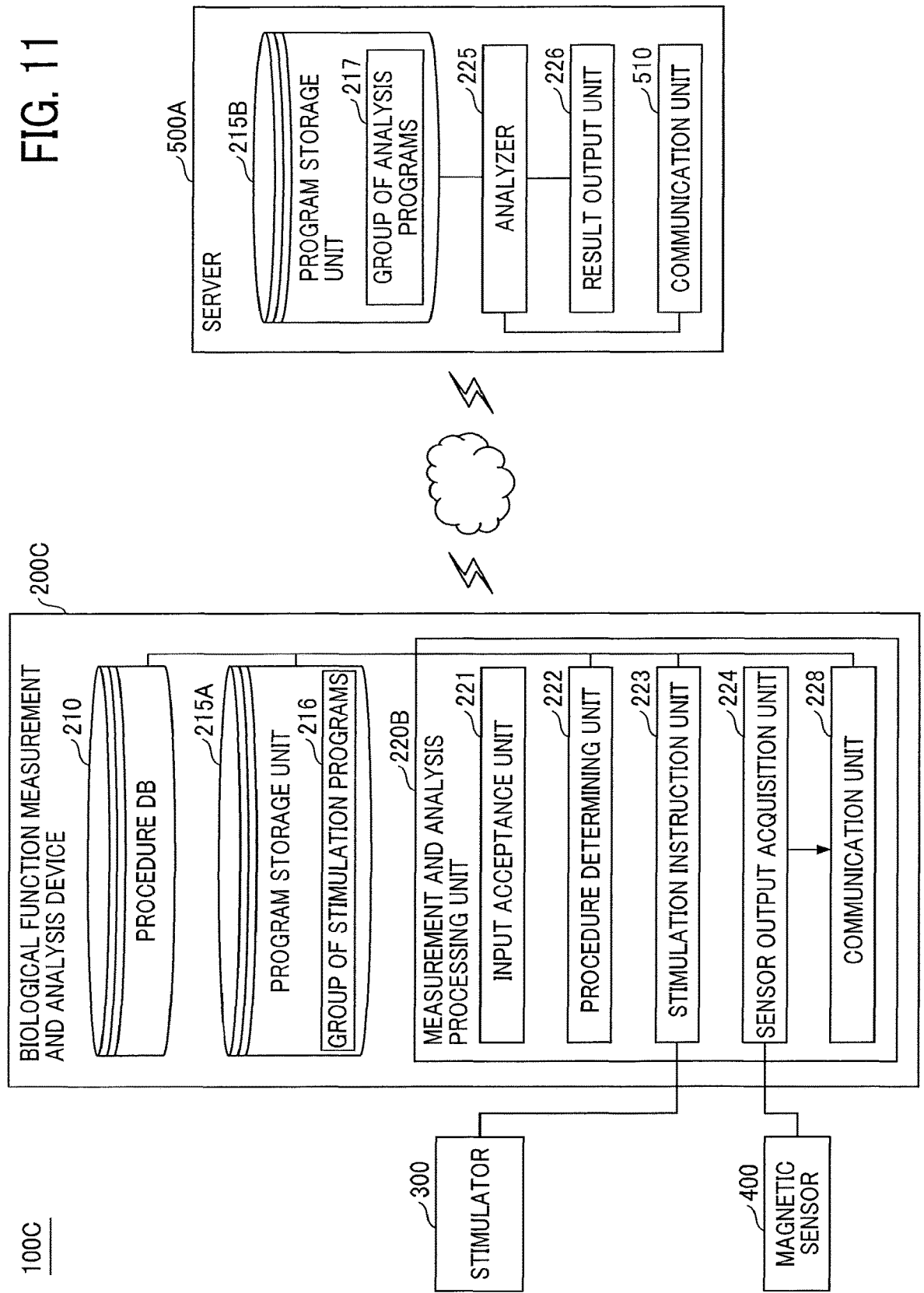
FIG. 11 is a diagram illustrating a biological function measurement and analysis system according to a fourth embodiment.

FIG. 11 is a diagram illustrating a biological function measurement and analysis system 100C according to the fourth embodiment. The biological function measurement and analysis system 100C according to the present embodiment includes a biological function measurement and analysis device 200C, the stimulator 300, the magnetic sensor 400, and a server 500A.

The biological function measurement and analysis device 200C according to the present embodiment includes the procedure DB 210, a program storage unit 215A in which the group of stimulation programs 216 is stored (that serves as a first program storage unit), and the measurement and analysis processing unit 220B. The measurement and analysis processing unit 220B includes the input acceptance unit 221, the procedure determining unit 222, the stimulation instruction unit 223, a sensor output acquisition unit 224, a communication unit 228. The communication unit 228 communicates with an external device including the server 500A.

The server 500A according to the present embodiment includes a program storage unit 215B in which the group of analytical programs 217 is stored (that serves as a second program storage unit), the analyzer 225, the result output unit 226, and the communication unit 510. The communication unit 510 communicates with an external device including the biological function measurement and analysis device 200C.

Once the selection of the function of the brain to be measured is accepted by the input acceptance unit 221, the biological function measurement and analysis device 200C according to the present embodiment accesses the procedure DB 210, and uses the procedure determining unit 222 to specify the measurement and analysis procedure data.

Once the measurement and analysis procedure data is specified, the biological function measurement and analysis device 200C according to the present embodiment extracts the stimulation program included in the group of stimulation programs 216 stored in the program storage unit 215A, and controls the stimulation instruction unit 223 to execute the extracted stimulation program.

In so doing, the biological function measurement and analysis device 200C may send the specified measurement and analysis procedure data to the server 500A through the communication unit 228.

Then, once the sensor output signal is obtained from the magnetic sensor 400 using the sensor output acquisition unit 224, the biological function measurement and analysis device 200C sends the sensor output signal to the server 500A through the communication unit 228.

Once the measurement and analysis procedure data is received, the server 500A uses the analyzer 225 to extract the analytical program from the group of analytical programs 217 stored in the program storage unit 215B, according to the measurement and analysis procedure data, and executes the extracted analytical program. Moreover, the server 500A controls the result output unit 226 to output the measurement results.

As described above, according to the present embodiment, the analyzer 225 that performs analytical processing and the program storage unit 215B in which the group of analytical programs 217 is stored are provided for the server 500A. Accordingly, the processes related to the analysis can be performed by the server 500A. Accordingly, with the present embodiment, the processing load of the biological function measurement and analysis device 200C can be reduced.

Numerous additional modifications and variations are possible in light of the above teachings. It is therefore to be understood that within the scope of the appended claims, the disclosure of the present disclosure may be practiced otherwise than as specifically described herein. For example, elements and/or features of different illustrative embodiments may be combined with each other and/or substituted for each other within the scope of this disclosure and appended claims.

Further, as described above, any one of the above-described and other methods of the present disclosure may be embodied in the form of a computer program stored on any kind of storage medium. Examples of storage media include, but are not limited to, flexible disks, hard disks, optical discs, magneto-optical discs, magnetic tape, nonvolatile memory cards, ROM, etc. Alternatively, any one of the above-described and other methods of the present disclosure may be implemented by ASICs, prepared by interconnecting an appropriate network of conventional component circuits, or by a combination thereof with one or more conventional general-purpose microprocessors and/or signal processors programmed accordingly.

The hardware platform includes any desired kind of hardware resources including, for example, a CPU, a random access memory (RAM), and a hard disk drive (HDD). The CPU may be implemented by any desired kind of any desired number of processor. The RAM may be implemented by any desired kind of volatile or non-volatile memory. The HDD may be implemented by any desired kind of non-volatile memory capable of storing a large amount of data. The hardware resources may additionally include an input device, an output device, or a network device, depending on the type of the apparatus. Alternatively, the HDD may be provided outside of the apparatus as long as the HDD is accessible. In this example, the CPU, such as a cache memory of the CPU, and the RAM may function as a physical memory or a primary memory of the apparatus, while the HDD may function as a secondary memory of the apparatus.

What is claimed is:

1. A biological function measurement and analysis system, comprising:

an input interface configured to accept selection of a biological function to be measured among a plurality of biological functions; and processing circuitry configured to access a memory in which is stored measurement and analysis procedure data including, for each of the plurality of biological functions, a set sequence of a plurality of pairs each including (1) a stimulation program containing a measurement procedure for measuring data of a reaction of a live subject caused by stimulation selected from a plurality of stimulation programs, and (2) an analytical program containing an analysis procedure for analyzing the measured data selected from a plurality of analytical programs, and extract the set sequence of the plurality of pairs corresponding to the selected biological function to be measured from the stored measurement and analysis procedure data, prior to stimulation of the live subject and measurement of the data of the reaction, wherein the analytical program in each of at least two pairs among the set sequence of the plurality of pairs is different from each other, the stored measurement and analysis procedure data further includes, for each of the plurality of biological functions, a value for execution procedure indicating an order in which the plurality of pairs is executed and another value indicating an interval between a timing at which a certain pair among the plurality of pairs is executed and a timing at which the next pair of the certain pair among the plurality of pairs is executed, and the processing circuitry is further configured to:

change at least one parameter of the next simulation program to be executed while keeping the type of stimulation the same under a condition that a value output as a result of executing an analytical program is equal to or greater than a predetermined threshold;

instruct an associated stimulator to output stimulation according to the extracted set sequence of pairs; and analyze a signal detected by a sensor in response to the output stimulation.

2. The biological function measurement and analysis system according to claim 1, wherein the stored measurement and analysis procedure data includes data indicating at least one pair in which at least one stimulation program of the plurality of stimulation programs used to control the stimulator to output the stimulation is stored in association with at least one analytical program of the plurality of analytical programs used to analyze the signal, and the processing circuitry is further configured to execute the at least one stimulation program, and execute the at least one analytical program.

3. The biological function measurement and analysis system according to claim 2, wherein the at least one pair comprises a plurality of pairs, and wherein the stored measurement and analysis procedure data includes data of the plurality of pairs and data indicating time intervals between the plurality of pairs.

4. The biological function measurement and analysis system according to claim 3, wherein the processing circuitry is further configured to change a parameter included in the at least one stimulation program of the plurality of stimulation programs included in a second pair of the plurality of pairs according to a result of execution of the at least one analytical program of the plurality of analytical programs included in a first pair of the plurality of pairs.

5. The biological function measurement and analysis system according to claim 4, wherein a type of stimulation caused by the at least one stimulation program of the plurality of stimulation programs associated with the at least one analytical program of the plurality of analytical programs included in the first pair of the plurality of pairs is identical to a type of stimulation caused by the at least one stimulation program of the plurality of stimulation programs included in the second pair of the plurality of pairs.

6. The biological function measurement and analysis system according to claim 1, further comprising:

the memory, in which the measurement and analysis procedure data is stored, the memory comprising a group of stimulation programs including the plurality of stimulation programs and a group of analytical programs including the plurality of analytical programs;

the sensor; and the stimulator.

7. The biological function measurement and analysis system according to claim 6, wherein the group of stimulation programs includes a program used to terminate stimulation output from the stimulator, and wherein the program used to terminate stimulation output is executed by the processing circuitry prior to the stimulation program used to output stimulation.

8. The biological function measurement and analysis system according to claim 6, further comprising:

a biological function measurement and analysis device including the processing circuitry; and a server including the memory and an analyzer.

9. The biological function measurement and analysis system according to claim 1, comprising:

a biological function measurement and analysis device including a first program storage, the processing circuitry, and the first program storage in which the group of stimulation programs is stored; and a server including a second program storage, in which the group of analytical programs is stored, and an analyzer.

10. The biological function measurement and analysis system according to claim 1, wherein the sensor is a magnetic sensor.

11. The biological function measurement and analysis system of claim 1, wherein the processing circuitry is further configured to extract the set sequence of pairs from the measurement and analysis procedure data based only on the selected biological function to be measured.

12. A method of measuring and analyzing a biological function, the method comprising:

accepting selection of a biological function to be measured among a plurality of biological functions;

accessing a memory in which is stored measurement and analysis procedure data including, for each of the plurality of biological functions, a set sequence of a plurality of pairs each including (1) a stimulation program containing a measurement procedure for measuring data of a reaction of a live subject caused by stimulation selected from a plurality of stimulation programs, and (2) an analytical program containing an analysis procedure for analyzing the measured data selected from a plurality of analytical programs; and extracting, from the memory, the set sequence of the plurality of pairs corresponding to the selected biological function to be measured from the stored measurement and analysis procedure data, wherein the analytical program in each of at least two pairs among the set sequence of the plurality of pairs is different from each other comprises at least two different analytical programs, and the stored measurement and analysis procedure data further includes, for each of the plurality of biological functions, a value for execution procedure indicating an order in which the plurality of pairs is executed and another value indicating an interval between a timing at which a certain pair among the plurality of pairs is executed and a timing at which the next pair of the certain pair among the plurality of pairs is executed, and the method further comprising:

changing at least one parameter of the next simulation program to be executed while keeping the type of stimulation the same under a condition that a value output as a result of executing an analytical program is equal to or greater than a predetermined threshold;

instructing an associated stimulator to output stimulation according to the extracted set sequence of pairs; and analyzing a signal detected by a sensor in response to the output stimulation.

13. A non-transitory computer-readable recording medium storing a program for causing a computer to execute a method, the method comprising:

accepting selection of a biological function to be measured among a plurality of biological functions;

accessing a memory in which is stored measurement and analysis procedure data including, for each of the plurality of biological functions, a set sequence of a plurality of pairs each including (1) a stimulation program containing a measurement procedure for measuring data of a reaction of a live subject caused by stimulation selected from a plurality of stimulation programs, and (2) an analytical program containing an analysis procedure for analyzing the measured data selected from a plurality of analytical programs; and extracting, from the memory, the set sequence of the plurality of pairs corresponding to the selected biological function to be measured from the stored measurement and analysis procedure data, wherein the analytical program in each of at least two pairs among the set sequence of the plurality of pairs is different from each other, and the stored measurement and analysis procedure data further includes, for each of the plurality of biological functions, a value for execution procedure indicating an order in which the plurality of pairs is executed and another value indicating an interval between a timing at which a certain pair among the plurality of pairs is executed and a timing at which the next pair of the certain pair among the plurality of pairs is executed, the method further comprising:

changing at least one parameter of the next simulation program to be executed while keeping the type of stimulation the same under a condition that a value output as a result of executing an analytical program is equal to or greater than a predetermined threshold;

instructing an associated stimulator to output stimulation according to the extracted set sequence of pairs; and analyzing a signal detected by a sensor in response to the output stimulation.

* * * * *